United States Patent
Sioshansi et al.

(10) Patent No.: US 6,471,630 B1
(45) Date of Patent: *Oct. 29, 2002

(54) TRANSMUTABLE RADIOTHERAPY DEVICE

(75) Inventors: Piran Sioshansi, Lincoln; Raymond J. Bricault, West Boylston, both of MA (US)

(73) Assignee: RadioMed Corporation, Tyngsboro, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/046,744

(22) Filed: Mar. 24, 1998

(51) Int. Cl.$^7$ ................................................. A61N 5/00
(52) U.S. Cl. ......................................................... 600/1
(58) Field of Search ......................................... 600/1–8

(56) References Cited

U.S. PATENT DOCUMENTS

| | | |
|---|---|---|
| 4,702,228 A | 10/1987 | Russell, Jr. et al. |
| 4,754,745 A | 7/1988 | Horowitz |
| 4,946,435 A | 8/1990 | Suthanthiran et al. ......... 600/3 |
| 5,030,195 A | 7/1991 | Nardi ............................. 600/7 |
| 5,059,166 A | 10/1991 | Fischell et al. ................. 600/3 |
| 5,342,283 A | 8/1994 | Good ............................. 600/8 |
| 5,395,300 A * | 3/1995 | Liprie ............................ 600/3 |
| 5,405,309 A | 4/1995 | Carden, Jr. ..................... 600/3 |
| 5,503,614 A | 4/1996 | Liprie ............................ 600/7 |
| 5,514,071 A * | 5/1996 | Sielaff, Jr. et al. .............. 600/3 |
| 5,575,749 A | 11/1996 | Liprie ............................ 600/3 |
| 5,624,372 A | 4/1997 | Liprie ............................ 600/3 |
| 5,637,073 A | 6/1997 | Freire ............................ 600/3 |
| 5,840,009 A * | 11/1998 | Fischell et al. ................. 600/3 |
| 5,897,573 A * | 4/1999 | Rosenthal et al. ............. 600/3 |
| 5,906,573 A * | 5/1999 | Aretz ............................. 600/3 |
| 6,024,690 A | 2/2000 | Lee et al. ...................... 600/3 |

FOREIGN PATENT DOCUMENTS

WO    WO 99/33063    7/1999

OTHER PUBLICATIONS

International Search Report of International Application No. PCT/US00/08948.
Eigler et al., "A $^{48}$ Vanadium Brachytherapy Source for Treatment of Coronary Artery Restenosis", *Vascular Brachytherapy*, Chapter 23, pp. 231–236, 1996.

* cited by examiner

*Primary Examiner*—Samuel G. Gilbert
(74) *Attorney, Agent, or Firm*—McDermott, Will & Emery

(57) ABSTRACT

A general purpose radiotherapy device can be fabricated to net or near-net shape and then made radioactive in a single activation step. The device is made at least partially of a transmutable material which is transformable to a radioisotope-containing material upon activation by an accelerated beam of charged particles, such as protons, deuterons or alpha particles. The transmutable material is preferably rhodium and the radioisotope-containing material is preferably palladium-103.

17 Claims, 7 Drawing Sheets

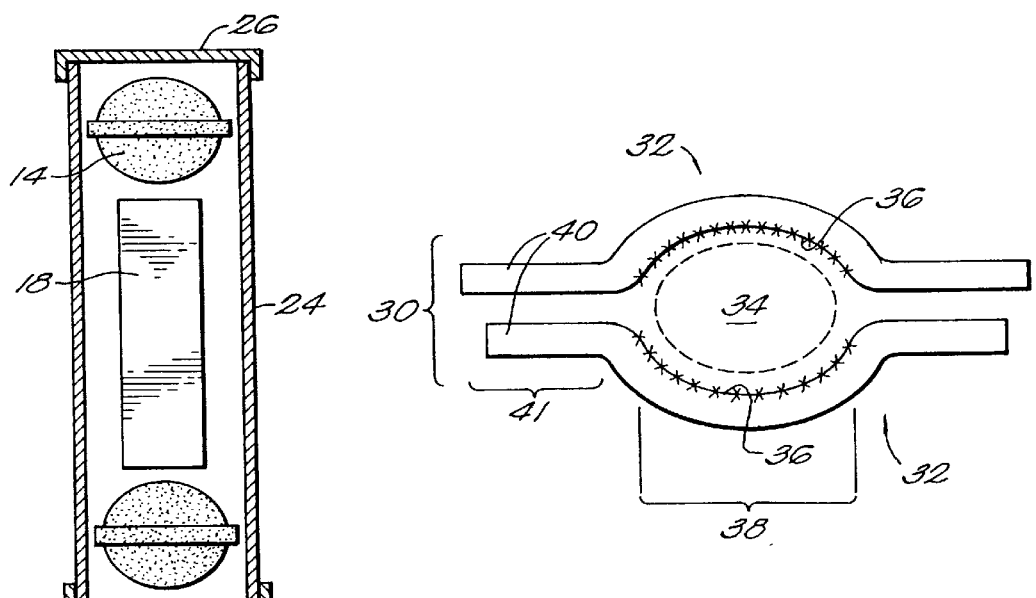
FIG. 1
(PRIOR ART)
FIG. 2
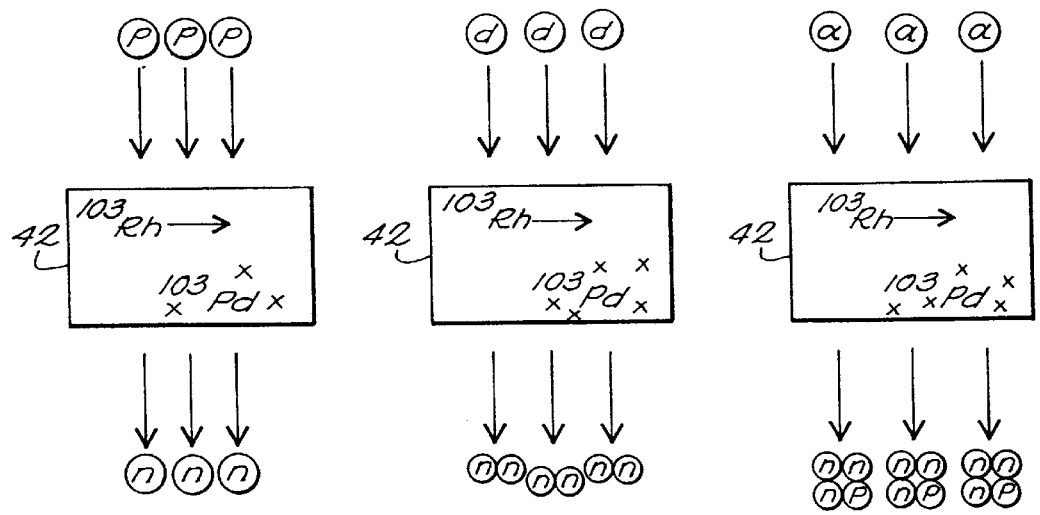
FIG. 3A   FIG. 3B   FIG. 3C

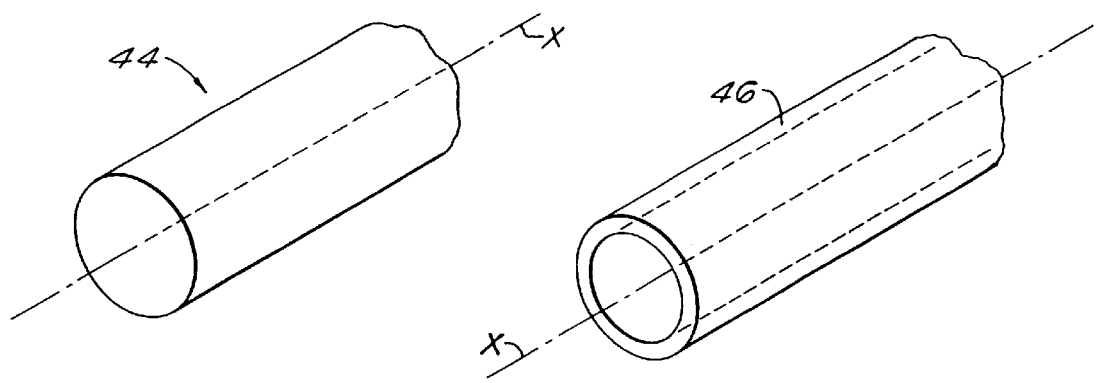
*FIG. 4*    *FIG. 5*
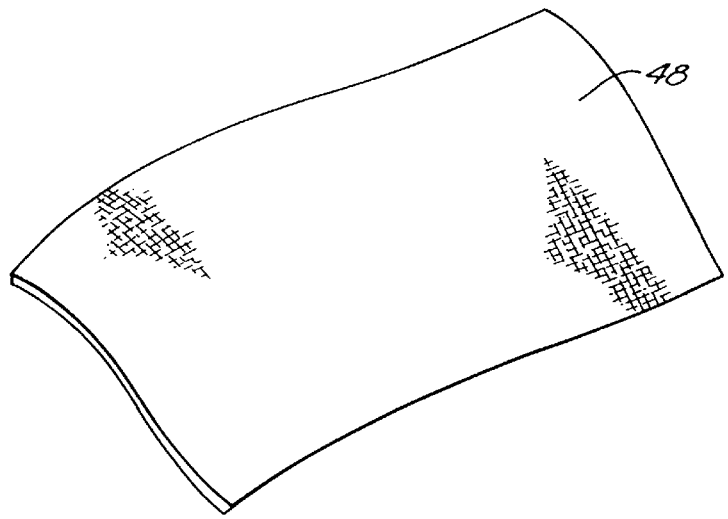
*FIG. 6A*
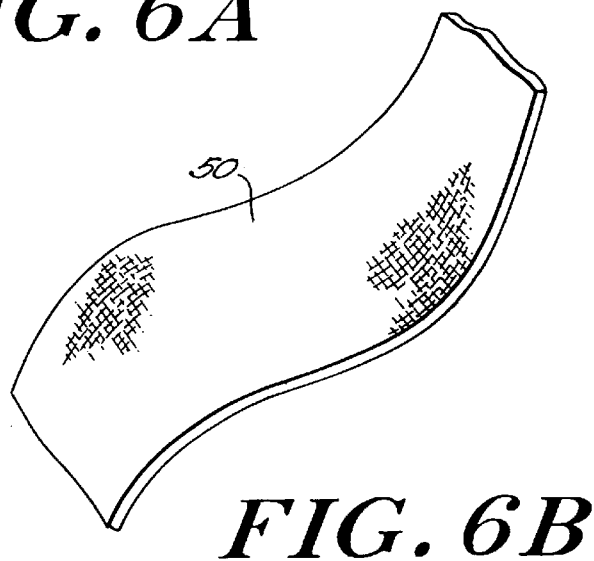
*FIG. 6B*

TRANSMUTABLE RADIOTHERAPY DEVICE

TECHNICAL FIELD

The invention is directed to implantable radiotherapy devices, and particularly to devices which can be made radioactive after being formed to a desired final or near-final shape

BACKGROUND OF THE INVENTION

Tumors, stenoses of biological conduits, and other proliferative tissue can be effectively treated with radiation, which is known to inhibit cellular proliferation. The mechanism by which radiation prevents such proliferative cellular response is by preventing replication and migration of cells and by inducing programmed cell death (apoptosis).

Cells are variably susceptible to radiation, dependent on the types of cells and their proliferative status. Rapidly proliferating cells are generally more radiation-sensitive, whereas quiescent cells are more radiation-tolerant. High doses of radiation can kill all functions of even quiescent cells. Lower levels can merely lead to division delays, but the desirable effect of reproductive death is still obtained. In this case, the cell remains structurally intact but has lost its ability to proliferate, or divide indefinitely.

Traditional high-dose external beam radiation treatment, and prolonged low dose rate, close-distance radiation treatment (brachytherapy), are well-established therapies for the treatment of cancer, a malignant form of cellular proliferation. In particular, attention is currently being directed to the practical aspects of the use of brachytherapy. These aspects are, of course, particularly significant when radioactivity is involved. A disease site in a patient may be exposed to radiation from an external beam, either as a stand-alone procedure or in conjunction with an operative procedure. Alternatively, the radioactivity may be incorporated into an implantable device. In the first case, a higher energy radiation source is used to achieve the necessary penetration of radiation into the tissue to be treated. As a result, other organs or tissue may be unnecessarily exposed to radiation, and safety, handling and logistics problems arise. In the second case, the implantable devices are typically quite expensive. In particular, if radioactivity is added to the source, the source may only be effective for radiotherapy during a relatively short period during which the radioactivity is provided at a useful (therapeutic) level. Depending on the radioisotope used, the decay time may be as short as hours, days or weeks.

The current state of the art brachytherapy for treatment of localized lesions such as tumors of, for example, the prostate, breast, brain, eye, liver, or spleen, employs radioactive, "sealed source" seeds. The term "sealed source", as used herein, means that radioisotopes incorporated into a device are integral with the device and cannot be dislodged or released from the host material of the device in the environment of usage. A typical sealed source seed includes a radiation source encapsulated within an impermeable, biocompatible capsule made of, for example, titanium, which is designed to prevent any leaching or release of the radioisotope. The seeds are approximately the size of a grain of rice (typically 0.81 mm in diameter by 4.5 mm long) and are implanted individually at a treatment site within and/or around a lesion, typically with a medium bore (18-gauge) delivery needle.

Disadvantages of the use of such seeds as radiotherapy devices include their nature as discrete, or point, sources of radiation, and the corresponding discrete nature of the dosages which they provide. In order to provide an effective radiation dose over an elongated or wide target area, the seeds should be uniformly and relatively closely spaced. The need to ensure accurate and precise placement of numerous individual radiation sources undesirably prolongs the surgical procedure, and hence the exposure of the surgical team to radiation. Moreover, the use of discrete seeds requires an elaborate grid matrix for their proper placement. This requirement is labor-intensive, and therefore costly. In addition, the discrete nature of the seeds renders them more susceptible to migration from their intended locations, thereby subjecting portions of the lesion, the treatment site, and surrounding healthy tissue to over- or under-dosage, reducing the effectiveness and reliability of the therapy.

Other disadvantages exist in radioactive seed therapy. Relatively few radionuclides are suitable for use in sealed-source seeds, because of limited availability of radioisotopes with the necessary combination of half-life, specific activity, penetration depth and activity, and geometry. In addition, the implantation of seeds generally requires a delivery needle with a sufficiently large bore to accommodate the seeds and may, in some cases, require an additional tubular delivery device. The use of a relatively large delivery needle during seeding may cause unnecessary trauma to the patient and displacement of the lesion during the procedure. Also, because of the risk of migration or dislodgement of the seeds, there is the risk that healthy tissues near or remote from the lesion site will be exposed to radiation from seeds which have become dislodged from their intended locations and possibly carried from the body within urine or other fluids. In addition, radioactive seed therapy is inadequate for treating certain types of intraluminal tissue proliferation, such as, for example, stenosed coronary arteries, and therefore a need exists for more suitable radiotherapy devices for such intraluminal brachytherapy applications.

Radiotherapy devices made of palladium-103 are desirable because palladium-103 has a half life of about 17 days and a photon energy of 20.1–23 KeV, which makes it particularly suitable for use in the treatment of localized lesions of the breast, prostate, liver, spleen, lung and other organs and tissues. Because palladium-103 is unstable and not naturally occurring in the environment, it must be manufactured, generally either by neutron activation of a palladium-102 target, or by proton activation of a rhodium target. In the neutron activation process, a palladium-102 isotope is exposed to a neutron flux in a nuclear reactor to convert palladium-102 to palladium-103. The efficiency of this conversion is dependent on the neutron flux and the duration of the bombardment in the reactor. The palladium-103 thus formed is fabricated into radioactive seeds. This approach is disclosed in, for example, U.S. Pat. No. 4,702,228 to Russell, Jr. et al.

The neutron activation approach is prohibitively expensive, as the natural abundance of palladium-102 is less than one percent. Enrichment of this isotope to even 20% levels is very costly. In addition, the utility of this process is unsatisfactory, as other isotopes of palladium and other elements, as well as impurities, may be formed and/or activated in the process and can alter or otherwise interfere with the desired radiation.

In the proton activation process, a rhodium-103 target is provided which is irradiated with a proton beam to transform a portion of the rhodium to palladium-103. This process requires that the rhodium-103 target be cooled and then irradiated until a sufficient amount of palladium-103 is obtained to enable chemical separation of the palladium from the rhodium. The rhodium target is then immersed in a strong acid to separate palladium-103 from rhodium-103. The palladium-103 radionuclides can now be used directly as radiation sources or formed into compounds-for later use. This material is generally absorbed into or otherwise incorporated into a non-radioactive carrier material which is then placed into a non-radioactive secondary container, such as a titanium can or shell, and sealed to form a radioactive seed. The secondary container may include some type of radiopaque marker to allow it to be radiographically visible. This approach is disclosed in, for example, U.S. Pat. No. 5,405,309 to Carden, Jr.

The proton activation approach also has disadvantages. Each step of the process requires a wet chemistry separation to isolate palladium-103 from rhodium-103, and each of these steps has a yield loss associated with it. The disadvantages of discrete seeds in brachytherapy applications have already been discussed.

U.S. Pat. No. 5,342,283 to Good discloses multi-layer radioactive microspheres and wires which are made by forming concentric radioactive and other coatings on a substrate. The radioactive coatings are made by various deposition processes, including ion plating and sputter deposition processes, as well as via exposure of an isotope precursor, such as palladium-102, to neutron flux in a nuclear reactor. The radioactive wires may have nonuniform distributions of radioactivity over their surfaces, as needed for a particular treatment.

A disadvantage of the Good radioactive devices is that they cannot be made economically or simply. As previously mentioned in connection with the creation of palladium-103 from palladium-102 using neutron flux, such processes are prohibitively expensive and require lengthy and costly wet chemistry separation steps to isolate the radioactive isotope from the non-radioactive precursor. Further, the coating methods disclosed by Good for making radioactive coatings are relatively complicated, multistep processes which are difficult to control. In addition, the multiple coatings of the Good devices may detach, deteriorate, flake, spall, peel, leach or otherwise degrade with time and/or exposure to bodily fluids, resulting in dissemination of radioactive and other materials into the body, with potentially harmful consequences.

It would therefore be an advancement in the art to provide a general purpose radiotherapy device which can be relatively easily and economically fabricated.

OBJECTS OF THE INVENTION

An object of the present invention is to provide a general purpose radiotherapy device which can be used to deliver a wide variety of radiation treatments.

Another object of the present invention is to provide a general purpose radiotherapy device which obviates the disadvantages of the prior art radiotherapy seeds and similar devices.

Another object of the present invention is to provide a general purpose radiotherapy device which can be fabricated to a desired net or near-net size and shape, and all or a portion of the device rendered radioactive in a relatively simple one-step activation process, without lengthy chemical separation steps to isolate the radioactive species from its nonradioactive precursor material.

And another object of the present invention is to provide a general purpose radiotherapy device made of a transmutable material which can be made radioactive upon exposure to an accelerated beam of charged particles.

Still another object of the invention is to provide a general purpose radiotherapy device which is made of a material which can be fabricated to net or near-net shape while in a non-radioactive state, and then made radioactive, and further formed or finished as needed in a radioactive state.

Another object of the invention is to provide a general purpose radioatherapy device which can be either temporarily or permanently implanted in a patient to deliver radiation in situ.

Still another object of the invention is to provide a general purpose radiotherapy device which provides radiation in a dose and distribution pattern that can be tailored or customized to any particular therapy requirement during fabrication and activation of the device.

Another object of the invention is to provide a general purpose radiotherapy device which emits radiation in a pattern that can vary over the length or breadth of the device and is not dependent solely on the shape of the device.

SUMMARY OF THE INVENTION

The radiotherapy device of the present invention provides an effective alternative to encapsulated radioactive seeds or sandwiched structures. The nature of the radiotherapy device disclosed herein allows it to be fabricated to virtually any desired net or near-net size and shape while it is in a non-radioactive state, and then all or a portion of the device rendered radioactive in a single activation step. The device can then be implanted into a patient either temporarily or permanently, with minimal loss of radioactivity and minimal radiation exposure to others. Alternatively, the device can be formed to an intermediate or near-net shape while in a non-radioactive state, and then all or a portion of the device made radioactive, and then the device can be formed as needed to a final shape while in a radioactive state.

The use of accelerated beam technology to make all or a portion of the device radioactive after it has been formed to net or near-net shape lowers the unit cost of the device, allows greater flexibility in the design and use of the device, and eliminates the need for laborious wet chemistry separation procedures. The device can be made to net or near-net shape in a variety of geometries, and all or any portion of the device can be made radioactive, so that it can be used in a wide variety of applications. Other advantages will be detailed more fully below.

According to the invention, there is provided a radiotherapy device for in situ delivery of radiation to a treatment site in a patient. At least a portion of the device is made of a transmutable material which is transformable to a radioisotope-containing material upon activation by an accelerated beam of charged particles. At least the transmutable portion of the device is formed to at least near-net shape.

The charged particles preferably have an energy of at least about 4 MeV and are preferably selected from the group consisting of protons, deuterons and alpha particles.

In a preferred embodiment, the transmutable material comprises rhodium and the radioisotope-containing material contains palladium-103. The transmutable portion of the device is formable either to a desired net shape prior to activation, or to a desired near-net shape prior to activation and to a desired net shape after activation, i.e., while in a radioactive state.

The device preferably emits radiation in a pattern having a shape which is determined at least in part by the distribution of the radioisotope-containing material on the surfaces of the transmutable portion of the device and not solely by the shape of the device. In one embodiment, the distribution of radioisotope-containing material is substantially constant; in another embodiment, it is variable.

In one embodiment, the device is in the form of an elongated element which can be substantially solid or tubular. The elongated element preferably has an aspect ratio of at least 3 to 1. In one preferred embodiment, the elongated element is in the form of a wire. The wire can include a transmutable portion at one or both ends thereof or at any intermediate portion. The elongated element can be formed into any two-dimensional or three-dimensional shape, such as a zig-zag or helix.

In another embodiment, the device is in the form of a two-dimensional sheet or a three-dimensional shape. In one preferred embodiment, the device is in the form of a spherically contoured plaque having a concave surface and a convex surface. At least a portion of the concave surface is activatable and includes palladium-103.

In still another embodiment, the device is in the form of a seed.

The source may be partially of a non-transmutable material which is preferably selected from the group consisting of non-transmutable metals, nonmetals, polymers and composite materials.

The device can further include a substantially radiation-transparent encapsulating material which is applied to at least a portion of the surface of the device. Alternatively, or additionally, the device can include a substantially radiation-transparent, non-radioactive agent applied to at least a portion of the surface of the device. The non-radioactive agent is preferably selected from the group consisting of therapeutic agents and lubricating agents.

The device can further include a radiopaque marker to make it visible under x-rays.

In one embodiment, the device is adapted for surgical fastening of tissue at a wound repair site and is preferably a device such as, for example, a staple, suture, clip, pin, nail, screw, plate, barb, anchor, or patch.

The device can be adapted for either temporary or permanent placement within the patient and may include one or more anchors suitable for such purpose.

According to another aspect of the invention, there is provided a method of delivering radiation in situ to a treatment site in a patient. The method comprises the steps of:
  a. Providing a radiotherapy device which is at least partially made of a transmutable material which is transformable to a radioisotope-containing material upon activation by an accelerated beam of charged particles, at least the transmutable portion being formed to at least near-net shape;
  b. Activating the transmutable portion of the device with a beam of charged particles at sufficient energy to form the radioisotope-containing material; and
  c. Placing the device at the treatment site in the patient so that the treatment site is exposed to the radioisotope-containing material.

The method can include the further step of forming the transmutable portion of the device to a desired net shape prior to activation, or to a desired near-net shape prior to activation and to a desired net shape after activation. In addition, the method can include the step of activating the transmutable portion of the device so that the device emits radiation in a pattern having a shape which is determined at least in part by the distribution of radioisotope-containing material on the surfaces of the transmutable portion of the device and not solely by the shape of the device. This distribution can be either substantially constant or variable. The method can include the further step of applying a substantially radiation-transparent encapsulating material to at least a portion of the surface of the device. In addition, or alternatively, the method can include the step of applying a substantially radiation-transparent, non-radioactive agent to at least a portion of the surface of the device. A radiopaque marker can also be incorporated into the device.

According to still another embodiment of the invention, a kit for delivering in situ a predetermined dose of radiation to a treatment site in a patient comprises a general purpose radiotherapy device, as described above, and a delivery vehicle for placing the device into the patient. In a preferred embodiment, the device is in the form of an elongated element and the delivery vehicle is a syringe or catheter.

BRIEF DESCRIPTION OF THE DRAWINGS

The foregoing and other features and advantages of this invention will be better understood from the following detailed description taken with the accompanying drawings, in which:

FIG. 1 is a cutaway view of a prior art radioactive seed made by exposing a non-radioactive palladium-102 target to neutron flux to obtain radioactive palladium-103, as known in the art;

FIG. 2 is a side elevational view of a radiotherapy device according to one aspect of the invention;

FIG. 3A is a schematic representation of the transmutation of rhodium-103 to radioactive palladium-103 by activation with a proton beam;

FIG. 3B is a schematic representation of the transmutation of rhodium-103 to radioactive palladium-103 with a deuteron beam;

FIG. 3C is a schematic representation of the transmutation of rhodium-103 to radioactive palladium-103 with an alpha particle beam;

FIG. 4 is a perspective view of a device in the form of a solid wire according to one embodiment of the invention;

FIG. 5 is a perspective view of a device in the form of a tube according to another embodiment of the invention;

FIG. 6A is a perspective view of a device in the form of a substantially two-dimensional flat sheet according to another embodiment of the invention;

FIG. 6B is a perspective view of a device in the form of a substantially three-dimensional shape according to another embodiment of the invention;

DETAILED DESCRIPTION OF THE INVENTION

Figure 8:
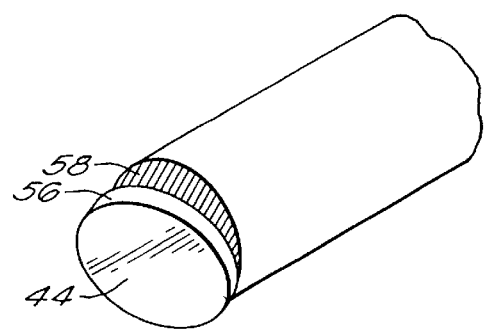
FIG. 8 is a cutaway view of a device in the form of a wire which includes a coating of a radiation-transparent, biocompatible encapsulating material, as well as at least one radiation-transparent, non-radioactive agent applied to the surface of the wire.

The invention is directed to radiotherapy devices which can be fabricated to net or near-net shape from a substantially non-radioactive material and then transformed, via exposure to a high-energy beam of charged particles, into a radioactive material. The device can be manufactured to net shape before it is made radioactive, and therefore it can be easily and economically worked, handled, transported and stored in a non-radioactive state. Alternatively, a device which is already radioactive can be formed to a final net shape just prior to use in order to customize a particular treatment. Significant advantages of the device of the present invention include the relative ease and economy with which it can be fabricated, the ability to fabricate the device either before or after radioactivation, and the ability to customize the device for a wide variety of radiotherapy applications as a result of the simplified fabrication and radioactivation process.

The term "implantable", as used herein, means any device which can be surgically introduced into a patient for either temporary or permanent placement. The term "transmutable" refers to the ability of a non-radioactive material to be converted, through nuclear transformation, into a radioisotope-containing material upon exposure to an accelerated beam of charged particles. The term "near-net shape", as used herein, refers to a near-final size and/or shape of the device for the intended treatment application but does not preclude additional, relatively minor formation steps, such as, for example, wire forming or cutting, sheet bending or cutting, punching, piercing, stamping, drawing, extruding, flattening, grinding, and the like, as well as surface treatments such as, for example, polishing, peening, knurling, scoring, abrading, and the like. The term "radioactivation", as used herein, refers to the process by which a transmutable, non-radioactive material is transformed to a radioisotope-containing material upon exposure to an accelerated beam of charged particles, such as protons, deuterons, or alpha particles, at an energy of greater than about 4 MeV.

The device is preferably made at least partially of a transmutable material which can be transformed into a radioisotope-containing material upon activation by an accelerated beam of charged particles. The transmutation process is effected in a nuclear accelerator or cyclotron and is highly efficient if a beam of sufficiently high-energy particles is used.

The transmutable portion of the device is preferably formed to at least near-net shape and in a preferred embodiment is made of rhodium, which is transmutable to radioactive palladium-103 upon exposure to an accelerated beam containing protons, deuterons or alpha particles.

The device can be fabricated to virtually any desired size and shape for the intended treatment application. For example, if an elongated wire is needed to provide a linear radiation source, a solid rhodium ingot can be drawn to the desired final dimensions of the filament. All or a portion of the wire can then be radioactivated upon exposure to an accelerated charged particle beam, effecting transmutation of the exposed rhodium to radioactive palladium-103. Alternatively, the rhodium ingot can be drawn to a desired intermediate size and/or shape, radioactivated in that intermediate state, and further shaped, formed or cut to the desired final dimensions just prior to implantation of the device in the patient.

Other geometries which may be useful for certain radiotherapy treatments include, for example, tubular structures, substantially flat thin sheets or foils which may be contoured around an organ, anatomic structure or lesion, and even discrete seeds, which can be conveniently formed by radioactivating elongated rhodium wires and then cutting them to the desired dimensions.

The device can be made entirely of a transmutable material, such as rhodium-103, or it may be made partially of a substantially non-transmutable material. The transmutable material can be attached to the nontransmutable material, such as by welding or other joining means, or it may be incorporated into portions of the nontransmutable material, such as by plating, diffusion, ion implantation, or other deposition or penetration techniques. Materials which are suitable for use as the non-transmutable portion of the device can include, for example, substantially non-transmutable metals, nonmetals, polymers, and composite materials.

Alternatively, the device can be made entirely of a transmutable material, with only a portion of the transmutable material being transformed, via irradiation with a beam of particles at a sufficient energy, to a radioisotope-containing material. Transmutation of a non-radioactive species to a radioactive species does not effect a total conversion of the non-radioactive species, and thus a portion of the non-radioactive species coexists with the radioactive species after transmutation has occurred. The ability to activate only a portion of the device, such as by setting the activating particle energy so that it does not effect full penetration of the material, or by fabricating the device so that it is thicker than any penetration depth of the charged particle beam, or by selective masking of portions of the device prior to and during activation, greatly enhances the customization potential and design flexibility of such devices.

If desired, a substantially radiation-transparent, biocompatible encapsulating material can be applied to at least a portion of the radioactive portion of the device to further encapsulate the radioactive portion of the device. The encapsulating material can be applied to the transmutable material prior to transmutation, or it can be applied to the radioisotope-containing material after transmutation. In addition, or alternatively, one or more substantially radiation-transparent, nonradioactive agents can also be applied to all or a portion of the surface of the device to deliver other benefits to the lesion or treatment site. Such agents can include, for example, therapeutic agents and lubricating agents. These agents can also be applied either before or after transmutation has occurred.

FIG. 1 illustrates a prior art radioactive seed, such as is manufactured by Theragenics Corporation (Norcross, Ga.). The radioactive seed comprises a titanium tube 24 containing within it two pellets 14 of radioactive palladium-103. The pellets are separated by a radiopaque lead marker 18. The tube is sealed and capped at the ends with welded caps 26. The seeds are approximately the size of a grain of rice and can be implanted in a patient at a treatment site with, for example, 18-gauge delivery needles. Such seeds can be made, for example, by the methods disclosed in U.S. Pat. No. 4,702,228 to Russell, Jr. et al. and U.S. Pat. No. 5,405,309 to Carden, Jr.

Besides the difficulty of fabrication of discrete radioactive seeds according to methods known in the art, the implantation of discrete seeds in the vicinity of a lesion to provide a suitable radiation dosage to the lesion without damaging surrounding healthy tissue is a tedious and labor-intensive process which cannot be reliably controlled to a satisfactory extent. Dosage control in three dimensions is relatively difficult when discrete seeds are used as the radiation delivery vehicle. The patient may suffer significant and unnecessary trauma, not only as a result of implantation of numerous discrete seeds, but also as a result of potential migration of some of those seeds, with attendant damage to adjoining healthy tissue, during the treatment period.

FIG. 2 illustrates a typical radiotherapy device 30 fabricated according to the present invention. The device 30 in this embodiment comprises a pair of shaped plates 32 which are made of a substantially non-radioactive transmutable material, such as rhodium. The plates 32 can be fabricated to a desired shape and size for the intended application. Lesion 34 is shown in phantom in FIG. 2 to illustrate a particular application for the device. In this application, the inner surfaces 36 of the central portions 38 of the plates could be activated in a high-energy charged particle beam, while legs 40 extending from either side of the central portions 38 of the plates could be masked during the activation process so as not to be transmutated to a radioactive species. The radioactive portions of the device would emit radiation in a converging pattern toward lesion 34.

Other geometries suitable for delivering a desired radiation dose might include, for example, a thin foil or sheet, or a wire mesh cage or basket, which can be preformed to surround a lesion of a particular size and shape; microfilaments or rods of constant or varying diameter to penetrate or otherwise provide radiation in a linear or radial radiation pattern at a treatment site; or a tubular structure sized to surround a lesion. For example, foils and sheets may be useful in the treatment of substantial areas, such as skin cancers. Such devices can be activated on one side and coated with a radiation-impervious layer on the other side to facilitate delivery of radiation in a single direction only. They can be formed as substantially two-dimensional patches, or they can be further formed before or after activation to complex three-dimensional shapes. Additional formation and contouring of such sheets can further focus or concentrate a pattern of radiation emitted therefrom. Other source geometries suitable for a particular application are considered to be within the scope of the invention.

FIGS. 3A–3C illustrate three preferred mechanisms for transforming rhodium to radioactive palladium-103. Rhodium and palladium atoms have atomic numbers 45 and 46, respectively. Although rhodium exists monoisotopically as rhodium-103, palladium has several isotopes, one of which is metastable palladium-103.

In FIG. 3A a rhodium target 42 is exposed to a high-energy beam of protons, preferably in the range of approximately 6–18 MeV. The transmutation reaction in the rhodium nucleus involves the capture of a single proton (p) and the emission of a single neutron (n). In FIG. 3B a rhodium target 42 is exposed to a high-energy beam of deuterons (nucleus of deuterium, containing one proton and one neutron). The transmutation reaction involves the capture of a deuteron (d) and the emission of two neutrons (n,n) from the rhodium nucleus to create palladium-103. In FIG. 3C a rhodium target 42 is exposed to a high-energy beam of alpha particles (helium nucleus, containing two protons and two neutrons. The transmutation reaction involves the capture of an alpha particle $\alpha$ and the emission of three neutrons (n,n,n) and one proton (p) from the rhodium nucleus to create palladium-103. In each case, the depth or extent of transmutation depends on the duration of exposure of at least the transmutable portion of the device to the irradiating beam, the energy of the beam, and the thickness of the transmutable portion of the device.

FIGS. 4, 5, 6A, 6B and 7 illustrate radiotherapy sources according to various alternative embodiments of the present invention. The source shown in FIG. 4 is in the form of an elongated element 44 which extends along a principal axis X and is preferably in the form of a drawn or extruded wire or rod made of a transmutable material, such as rhodium.

Exposure of the wire 44 to a high-energy beam of charged particles effects transmutation of a portion of the rhodium to palladium-103. The depth of penetration of a charged particle is a function of the energy of the particle. For example, at a particle energy of about 18 MeV, transmutation depths may be on the order of approximately 500 microns. If the diameter of a wire, or the thickness of a sheet or plaque, is less than approximately 500 microns, transmutation of the entire bulk of the device may occur upon exposure to charged particles at this energy. However, if the device diameter or thickness dimension is greater than approximately 500 microns, only a surface transformation will occur upon activation at this energy, and a core portion of the device will remain in the form of non-radioactive rhodium. Alternatively, a portion of the device may be masked or otherwise shielded from exposure to the charged particle beam, so that only the unmasked or unshielded (i.e., exposed) portions will be transformed, upon beam exposure, to palladium-103.

The device shown in FIG. 5 is a tube 46 which may be used to surround a lesion or region of tissue to be treated. Irradiation and transmutation of a tube of rhodium would typically be from the outside of the device in toward the central axis X. Other exposure and/or masking schemes may be used to provide a customized transmutation of the material of the device, thereby providing a customized radiation pattern from it.

FIG. 6A illustrates a substantially thin flat sheet or foil 48 which may be fabricated to surround, cover or otherwise closely conform to a lesion to be treated. Thin flat sheets may be particularly advantageous in certain applications, as they can be preformed and easily stored in a non-radioactive state until needed. Once activated, they can be further formed as needed, possibly even in situ, to conform to the contour of the lesion or tissue to be treated.

FIG. 6B illustrates a substantially two-dimensional sheet formed into a substantially three-dimensional complex shape 50, as needed, for example, to conform to an irregularly-shaped lesion or treatment area. The sheet may be formed to near-net shape and then radioactivated, or it may be radioactivated and then formed into a final net shape.

Figure 7:
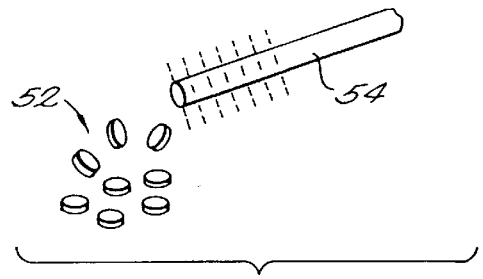
FIG. 7 is a perspective view of a device in the form of a seed according to another embodiment of the invention.

FIG. 7 illustrates a collection of radioactive seeds 52 made according to one aspect of the invention. Unlike the prior art seeds, which are a composite of pellets of radioactive material encased in a non-radioactive titanium shell, the seeds 52 of the present invention can be made directly from rhodium wires 54 which have been radioactivated and then cut to the desired seed dimensions just prior to implantation. Alternatively, the rhodium wires can be cut to desired lengths and the rhodium seeds thus formed stored in a non-radioactive state for later radioactivation. With either method, many costly fabrication steps are avoided in the manufacture of radioactive seeds using the transmutation techniques disclosed herein.

The radiotherapy device can be further treated with a substantially radiation-transparent, biocompatible encapsulant 56 over at least a portion of its surface, as illustrated in FIG. 8. The purpose of the encapsulant is to provide an additional safeguard to prevent leaching of any residual radioactivity from the device after transmutation. The encapsulant coating 56 may be applied to all or a portion of the device, illustrated as a wire 44, either pre- or post-transmutation and may comprise, for example, a polymer, metal, nonmetal, or ceramic. Typical techniques for applying the encapsulant include, for example, plating, sputtering, evaporation deposition, ion plating, plasma spray deposition, flame spray deposition, and chemical vapor deposition. Typical coating thicknesses may range from about 50 Angstroms to about 250 micrometers.

It may be also desirable to apply one or more substantially radiation-transparent, non-radioactive agents 58 over at least a portion of the surface of the device in order to deliver a non-radioactive treatment with the radiation. Such agents can include, for example, therapeutic agents, chemical agents, thermal agents, biological agents such as proteins and growth factors, lubricants or other friction-reduction agents, and other agents useful in various therapies. These agents can be applied either directly onto the transmutable material of the device, to the nontransmutable material of the device if such a substrate material forms part of the device, or onto the encapsulant coating 56. Such agents may be applied, for example, by such processes as immersion of the device in the desired medium, chemical grafting, plasma coating, plasma-assisted coating, plasma decomposition coating, vacuum coating (such as by evaporation, sputtering, ion implantation, and ion beam sputtering), plating, chemical vapor deposition, chemical reaction bonding, suspension drying, and the like.

Either or both types of coatings can be applied to the device, or respective portions of the device, as needed.

Figure 9A:
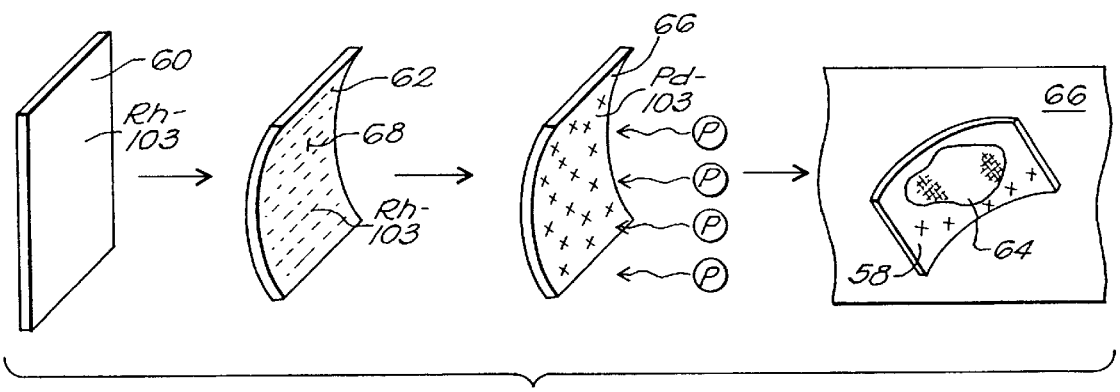
FIG. 9A is a flow diagram illustrating a method of delivering radiation to a localized lesion using a radiotherapy device fabricated according to one aspect of the invention.

FIG. 9A illustrates the steps of a method for treating a localized lesion or disease site in a patient using the techniques of the present invention. A rhodium sheet 60 is provided and formed into a desired shape and size. In this illustration, a flat sheet or foil of rhodium is formed into a contoured patch 62 which is dimensioned to surround or closely conform to a lesion 64 within a patient 66. The rhodium sheet 60 is then exposed to an activating beam of charged particles, such as a proton beam, at an energy level of between about 4 and 18 MeV. As illustrated in FIG. 9A, the device may be exposed to the charged particle beam only on one side or in a restricted area, if transmutation of only a portion of the device is desired. In this instance, the concave surface 68 of the sheet is irradiated with protons and transmutated to palladium-103, so that radiation can be emitted from the concave surface toward and into the lesion 64 upon implantation of the device into the patient, with minimal radiation exposure of surrounding healthy tissue.

Figure 9B:
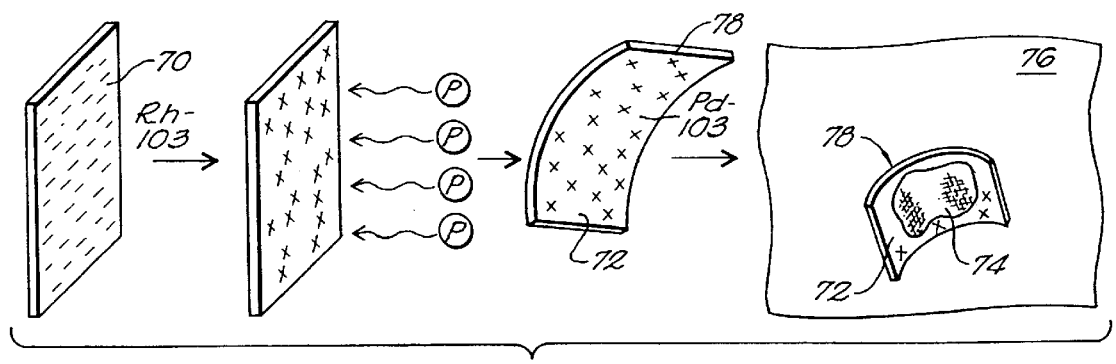
FIG. 9B is a flow diagram illustrating an alternate method of delivering radiation to a localized lesion using a radiotherapy device fabricated according to another aspect of the invention.

FIG. 9B illustrates steps of a method for treating a localized lesion or disease site within a patient which requires a radioactive, contoured, three-dimensional shape. In this illustration, a flat sheet made of rhodium 70 is radioactivated in a charged particle beam, preferably on a single surface 72 which will be the surface closest to the lesion to be treated 74 in a patient 76, and then formed into a complex contoured shape 78 while in a radioactive state. The desired net shape and size of the device can be determined from mapping techniques known in the art for mapping the dimensions of lesions within tissue.

If desired, the devices illustrated in FIGS. 9A and 9B can be further treated with a radiation-impervious material on the unactivated side, to minimize radiation emission in a direction away from the region or tissue to be treated.

Figure 10:
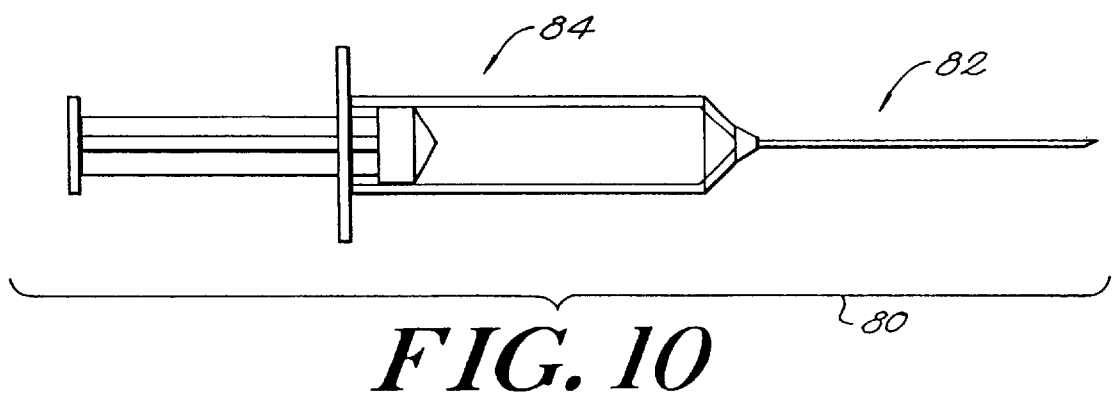
FIG. 10 is a side elevational view of a radiotherapy delivery kit according to another aspect of the invention.

FIG. 10 illustrates a kit for delivering a predetermined dose of radiation to a disease site or lesion within a patient. The kit 80 includes a radiotherapy device in the form of a substantially elongated element 82, such as a wire which can be solid or tubular, as described herein, and a delivery vehicle, such as a syringe 84 or the like, for inserting the elongated element into the patient at or near the treatment site. The radiotherapy device is provided in a form which is suitable for the particular application, such as treatment of prostate tumors. It is made substantially of a transmutable, non-radioactive material, such as rhodium, and can be activated upon exposure to an accelerated charged particle beam to become radioactive.

The use of radioactive wires for the treatment of proliferative tissue is known to be an advancement over the current seeding techniques. The radiation dosage obtainable using radioactive wires can be either substantially uniform or variable over the entire length of the wire. In any event, the dosage can be discriminately applied based upon the specific therapy requirements by tailoring the shape of the device and the radiation pattern emitted from it. In addition, the wires can be positioned accurately and reliably, without migration or dislodgement of the radiation source from its intended position.

The significant advantage of the present invention is the relative ease with which such devices can be manufactured. Near-net shape devices of any desired size and shape can be fabricated and then made radioactive in a single activation step, without the need for elaborate chemical separation processes. Moreover, the ability to fabricate the devices to at least near-net shape before radioactivation provides tremendous design flexibility for the device and provides a means of treating a wide variety of disease sites in a wide variety of locations and stages of development.

Figure 11:
FIG. 11 is a side elevational view of an elongated radiotherapy device having a substantially zig-zag two dimensional shape.
Figure 13:
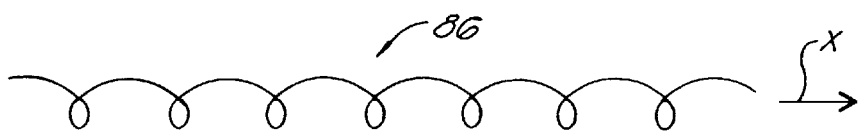
FIG. 13 is a side elevational view of an elongated radiotherapy device having a substantially coiled geometry.
Figure 12:
FIG. 12 is a side elevational view of an elongated radiotherapy device having a substantially serpentine two dimensional shape.

The devices can be either substantially solid in cross-section, or tubular, or porous, or of any other geometry which facilitates the administration of a therapeutic dose of radiation to a localized lesion. A wire can be cut to various lengths, either prior to or after high-energy beam radioactivation, to suit the particular application. For example, a preferred length of radioactive wire or filament for use in prostate tumor therapy is between about 10 and 60 mm, and a preferred diameter is about 0.20 mm. As illustrated in FIGS. 11 and 12, a wire 86 can be formed, for example, into a two-dimensional zig-zag or serpentine shape, or into a three-dimensional helix or coil, as illustrated in FIG. 13. The device may be rendered radioactive over a portion or the entirety of its length, as needed. It may be formed to near-net shape first, and then radioactivated, or radioactivated first and then formed to its final net shape.

Figure 14:
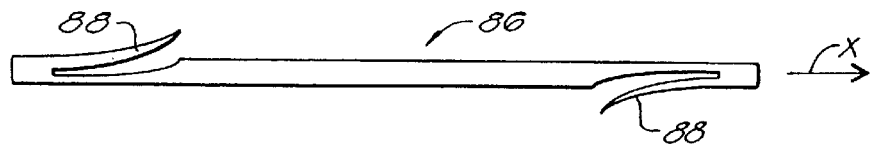
FIG. 14 is a side elevational view of an elongated radiotherapy device having a barbed anchoring element at each end of the device.
Figure 15:
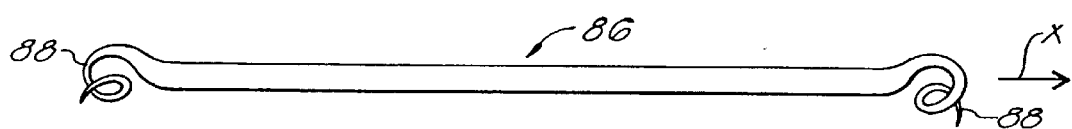
FIG. 15 is a side elevational view of an elongated radiotherapy device having a coiled anchoring element at each end of the device.

The device can be permanently or temporarily implanted in the patient. It can also be removed from the patient after radiotherapy treatment has been completed, undergo reactivation in an irradiating charged particle beam, and reimplanted to deliver radiation in another application. As shown in FIGS. 14 and 15, the device 86 can include means, preferably in the form of one or more anchors or barbs 88 of various forms known in the art, for fixation of the device in the host tissue so that it remains in place after implantation for the duration of the radiation treatment, and possibly indefinitely.

Two applications in which the radiotherapy device of the present invention are of particular interest are the treatment of prostate tumors, both benign and malignant, and the treatment of ophthalmic lesions, such as intraocular melanoma, retinoblastoma, and macular degeneration. Other applications which may also be suitable for treatment with the device of the present invention include the treatment of breast, spleen, liver, lung and brain tumors, as well as other localized tumors.

For example, in the case of radiotherapy of prostate tumors, the radiotherapy device of the present invention may comprise a relatively thin, narrow, elongated member, such as a relatively fine-gauge filament, which can be inserted into or around the tumor. The filament can be substantially solid in cross-section, or it can be tubular. The device can be fabricated into any two- or three-dimensional structure prior to or after radioactivation with a charged particle beam. It can be made fully or partially radioactive, depending on the duration of exposure to the beam and on the existence of any masking or other shielding of any portion of the source. The radiation pattern from such a device thus can generally follow the shape of the device, or it can be tailored to meet specific therapy requirements.

For the treatment of, for example, tumors of the prostate, it is preferred to employ a solid or tubular rhodium wire which is transmutable to palladium-103 upon irradiation with protons, deuterons or alpha particles at an energy level of at least 4 MeV. Palladium-103 is already used in radioactive seeds used to treat prostate tumors, and thus its behavior in, and suitability for, this application is well-documented. In a preferred embodiment, palladium-103 is provided in the form of 20-, 40- and 60 mm wire segments to establish an activity per unit length for each wire which corresponds to the discrete seed activity, or seed source strength, provided by this radioisotope in seed form.

Figure 16A:
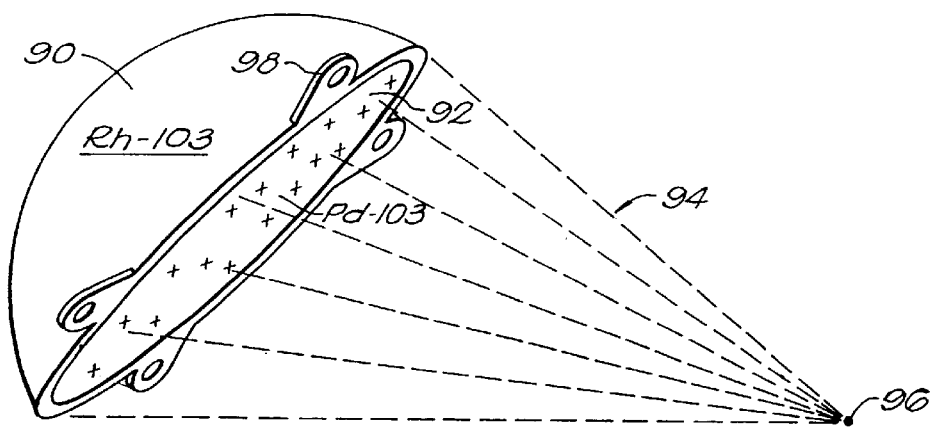
FIG. 16A is a perspective view of a hemispherical plaque useful in the treatment of ocular lesions.
Figure 16B:
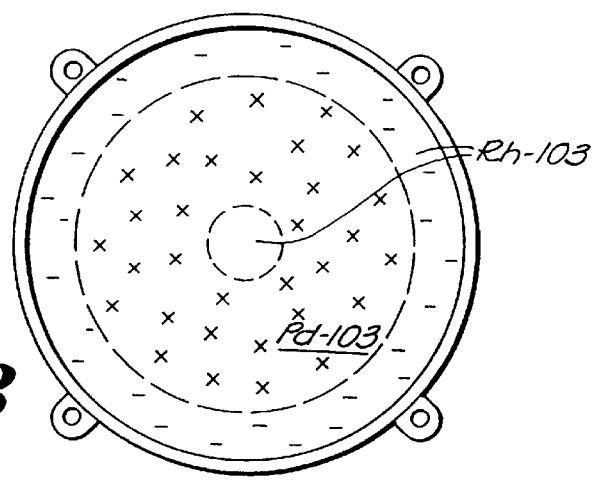
FIG. 16B is an axial view of a hemispherical plaque which has been selectively activated to provide an annular radioactive portion.
Figure 16C:
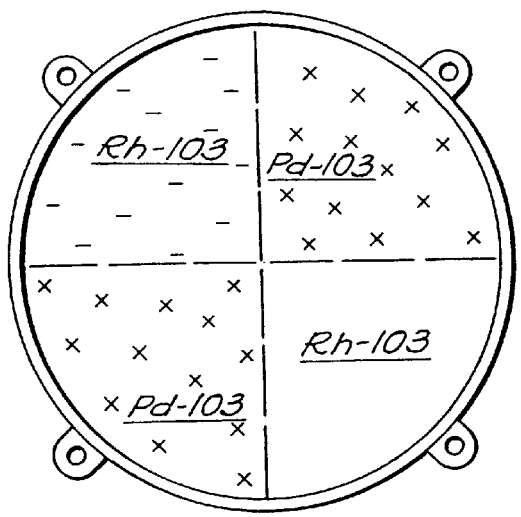
FIG. 16C is an axial view of a hemispherical plaque which has been selectively activated to provide sector-shaped radioactive portions.

In the case of radiotherapy of ophthalmic lesions, the radiotherapy device of the present invention may comprise a hemispherical plaque 90, illustrated in FIGS. 16A–16C, having a substantially spherically contoured shape with a predetermined radius of curvature. Transmutation of the material of the plaque, for example, the concave surface 92 of the plaque, via exposure to a high-energy charged particle beam, will produce a radioactive surface that will define a radiation pattern 94 which converges toward a focal point or region 96 located within the lesion or tissue to be treated. As previously mentioned, selective exposure of the plaque to the accelerated charged particle beam, as well as selective masking of portions of the plaque, can produce, for example, annular or sector-shaped radioactive portions which emit radiation in corresponding patterns, as shown in FIGS. 16B and 16C, respectively. It may be desirable to provide a radiation-impervious coating, such as a layer of gold, on the non-radioactive surface of the device, such as on the convex surface of the plaque, to prevent unwanted irradiation of the skull behind the eye from the radioisotope-containing concave surface of the plaque.

The plaque can include one or more anchors 98 in the form of eyelets or like structures which permit attachment of the plaque to tissue.

Figure 17:
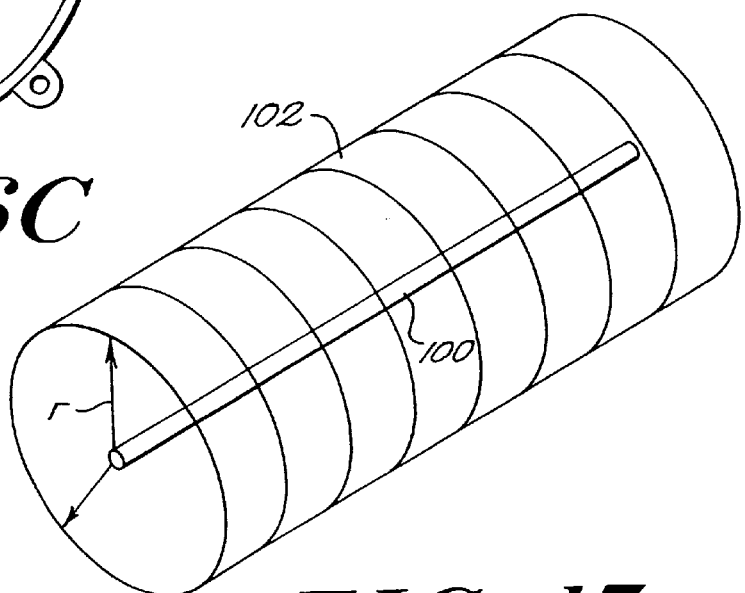
FIG. 17 is a perspective view of an elongated element which has been activated along its length to provide a substantially uniform, constant-radius radiation pattern.
Figure 18:
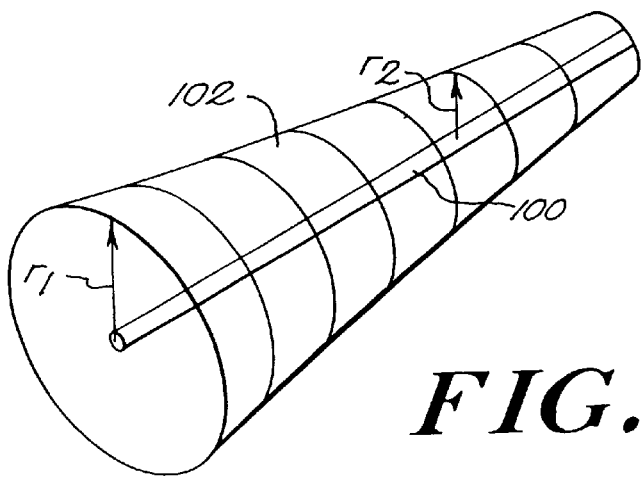
FIGS. 18 and 19 are perspective views of elongated elements which have been activated along their respective lengths to provide varying radiation patterns.
Figure 19:
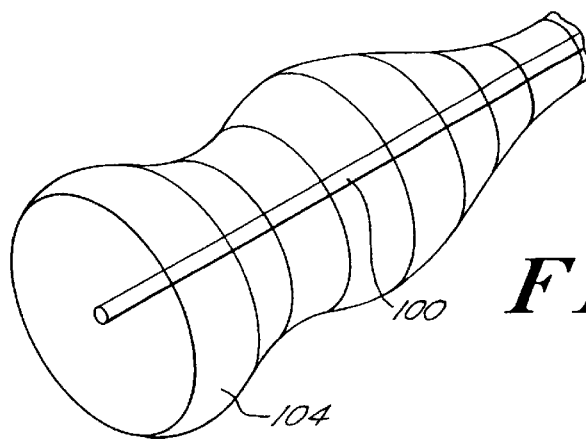
Figure 20A:
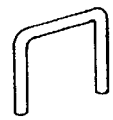
FIGS. 20A–20G are perspective views of various surgical fastening devices made of a transmutable material which is activatable to a radioisotope-containing material according to the invention.
Figure 20B:
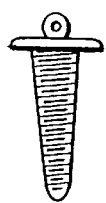
Figure 20D:
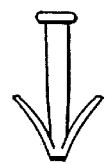
Figure 20C:
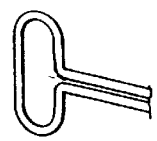
Figure 20E:
Figure 20F:
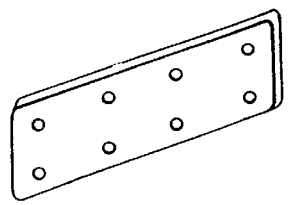
Figure 20G:
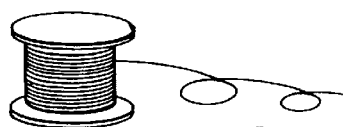

Selective masking and/or activation of portions of a device can produce devices which emit radiation in a characteristic pattern which is not solely determined by the shape of the device. For example, a selectively activated rhodium wire 100 may produce a constant-radius radiation pattern 102 along its length, as shown in FIG. 17, or a variable-radius radiation pattern along its length, as shown in FIGS. 18 and 19.

Surgical fastening devices, including, for example, sutures, staples, clips, pins, nails, screws, plates, barbs, anchors, and patches, can also be easily fabricated from rhodium and activated to become partially or wholly radioactive as described herein. Such devices are particularly useful in wound site repair. Examples of such devices are illustrated in FIGS. 20A–20G.

The use of accelerated beam technology to transform non-radioactive, transmutable materials to radioactive materials provides several advantages, such as ease of manufacturability of the device and the ability of the device to be reactivated with successive accelerated beam treatments as needed without adversely affecting the structural integrity of the device. The ability to manufacture near-net shape devices from transmutable, non-radioactive materials, and transform them to radioactive devices, in a single fabrication step, is a substantial advantage of the present invention which is not addressed or provided in the prior art.

With the present invention, any desired configuration of the device is obtainable, and any desired radiation is obtainable with the appropriate masking of portions of the device while exposed to the high-energy beam. A significant advantage of fabricating the radiotherapy source from a transmutable material is that fabrication of the device to any desired size, shape or configuration can be done while it is nonradioactive. The device can then be made radioactive in its final form via exposure to a high-energy charged particle beam. The net shape of the device as fabricated will be the net shape of the device in its final, ready-to-use form.

The nuclear transmutation technique for fabricating net-shape and near-net shape radiotherapy devices eliminates many costly process steps and allows the device to be fabricated easily and economically before it is rendered radioactive. In addition, the device can be exposed to an accelerated charged particle beam as many times as is required to effect transmutation of the material of the device. This feature eliminates storage and shelf-life problems associated with prior art radioactive devices. Should the device not be used for treatment during the half-life of the radioactive material, it can simply be reactivated.

Although a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. An interstitial radiotherapy device for in situ delivery of radiation to tumorous tissue at a treatment site in a patient, at least a portion of the device being made of rhodium which is transformable to palladium-103 upon activation by an accelerated beam of particles including protons having an energy of at least 4 MeV, wherein at least the rhodium portion of the device is formed to at least near-net shape, wherein the device is in the form of a wire.

2. A radiotherapy device according to claim 1, wherein at least the rhodium portion of the device is formable either to a desired net shape prior to activation, or to a desired near-net shape prior to activation and to a desired net shape after activation.

3. A radiotherapy device according to claim 2, wherein the wire is formed into a spiral shape.

4. A radiotherapy device according to claim 2, further comprising a substantially radiation-transparent encapsulating material applied to at least a portion of the surface of the device.

5. A radiotherapy device according to claim 4, further comprising a substantially radiation-transparent, non-radioactive agent applied to at least a portion of the surface of the device.

6. A radiotherapy device according to claim 5, wherein said non-radioactive agent is selected from the group consisting of therapeutic agents and lubricating agents.

7. A radiotherapy device according to claim 2, further comprising a radiopaque marker.

8. A radiotherapy device according to claim 2, wherein the device is adapted for substantially permanent implantation in a patient.

9. A radiotherapy device according to claim 2, wherein the device is adapted for temporary placement in a patient.

10. A method of delivering radiation to tumorous tissue at a treatment site in a patient, comprising the steps of:

a. providing an interstitial radiotherapy device in the form of a wire for in situ delivery of radiation to tumorous tissue at a treatment site in a patient, at least a portion of the device being made of rhodium which is transformable to palladium-103 upon activation by an accelerated beam of charged protons, wherein at least the rhodium portion of the device is formed to at least near-net shape;

b. activating the device with a beam of charged protons having an energy of at least 4 MeV to form palladium-103; and c. placing the device in or near tumorous tissue at the treatment site in the patient so that the tumorous tissue is exposed to the palladium-103.

11. A method according to claim 10, comprising the further step of:

d. forming the rhodium portion of the device to a desired net shape prior to activation, or to a desired near-net shape prior to activation and to a desired net shape after activation.

12. A method according to claim 11, comprising the further step of:

e. activating the device so that the device emits radiation in a pattern having a shape which is determined at least in part by the distribution of palladium-103 on the device and not solely by the shape of the device.

13. A method according to claim 12, wherein the wire is formed into a spiral shape.

14. A method according to claim 12, comprising the further step of:

f. applying a substantially radiation-transparent encapsulating material to at least a portion of the surface of the device.

15. A method according to claim 14, comprising the further step of:

g. applying a substantially radiation-transparent, non-radioactive agent to at least a portion of the surface of the device.

16. A method according to claim 15, wherein said non-radioactive agent is selected from the group consisting of therapeutic agents and lubricating agents.

17. A method according to claim 12, comprising the further steps of providing a radiopaque marker and incorporating the marker into the device.

* * * * *

UNITED STATES PATENT AND TRADEMARK OFFICE
CERTIFICATE OF CORRECTION

PATENT NO. : 6,471,630 B1
DATED : October 29, 2002
INVENTOR(S) : Piran Sioshansi et al.

It is certified that error appears in the above-identified patent and that said Letters Patent is hereby corrected as shown below:

Column 15,
Line 16, after "beam of", insert -- charged --.

Signed and Sealed this

First Day of April, 2003

JAMES E. ROGAN
*Director of the United States Patent and Trademark Office*